(12) United States Patent
Bourne

(10) Patent No.: US 7,849,875 B2
(45) Date of Patent: Dec. 14, 2010

(54) CHECK VALVE

(75) Inventor: John M. Bourne, Tustin, CA (US)

(73) Assignee: Alcon, Inc., Hunenberg (CH)

( * ) Notice: Subject to any disclaimer, the term of this patent is extended or adjusted under 35 U.S.C. 154(b) by 132 days.

(21) Appl. No.: 11/831,204

(22) Filed: Jul. 31, 2007

(65) Prior Publication Data

US 2009/0032123 A1  Feb. 5, 2009

(51) Int. Cl.
*F16K 17/30* (2006.01)
*A61M 1/00* (2006.01)

(52) U.S. Cl. .......................................... 137/517; 604/27

(58) Field of Classification Search ................ 137/496, 137/517; 604/37, 113, 291
See application file for complete search history.

(56) References Cited

U.S. PATENT DOCUMENTS

| | | | |
|---|---|---|---|
| 121,697 A * | 12/1871 | Wheatland ................. | 137/517 |
| 294,334 A * | 2/1884 | Reed et al. ................. | 137/517 |
| 351,159 A * | 10/1886 | Brengel ..................... | 137/517 |
| 865,631 A | 9/1907 | Cotter | |
| 2,121,936 A * | 6/1938 | Rosswell ................... | 137/496 |
| 2,536,836 A | 1/1951 | Bowling | |
| 2,623,725 A | 12/1952 | Sands | |
| 3,085,589 A | 4/1963 | Sands | |
| 3,191,807 A | 6/1965 | Rodrigues | |
| 3,336,942 A | 8/1967 | Garland et al. | |
| 3,561,471 A | 2/1971 | Sands | |
| 3,589,363 A | 6/1971 | Banko et al. | |
| 3,693,613 A | 9/1972 | Kelman | |
| 3,756,270 A | 9/1973 | Fonseca et al. | |
| 3,818,913 A | 6/1974 | Wallach | |
| 4,018,247 A | 4/1977 | Carr | |
| 4,030,520 A | 6/1977 | Sands | |
| 4,155,374 A | 5/1979 | Diehl | |
| 4,156,187 A | 5/1979 | Murry et al. | |
| 4,168,707 A | 9/1979 | Douvas et al. | |
| 4,223,676 A | 9/1980 | Wuchinich et al. | |
| 4,246,902 A | 1/1981 | Martinez | |
| 4,274,411 A | 6/1981 | Dotson, Jr. | |
| 4,380,911 A | 4/1983 | Zumbiel | |
| 4,493,694 A | 1/1985 | Wuchinich | |
| 4,515,583 A | 5/1985 | Sorich | |
| 4,570,669 A | 2/1986 | Pauliukonis | |
| 4,589,415 A | 5/1986 | Haaga | |
| 4,609,368 A | 9/1986 | Dotson, Jr. | |
| 4,655,247 A | 4/1987 | Westra et al. | |
| 4,657,490 A | 4/1987 | Abbott | |
| 4,668,231 A | 5/1987 | deVries et al. | |
| 4,784,652 A | 11/1988 | Wikstrom | |
| 4,797,098 A | 1/1989 | Kawata | |

(Continued)

FOREIGN PATENT DOCUMENTS

EP    1199054 A1    4/2002

(Continued)

OTHER PUBLICATIONS

John M. Bourne, Spring-Less Check Valve for a Handpiece, U.S. Appl. No. 12/237,468, filed Sep. 25, 2008 (18 pages).

*Primary Examiner*—John Rivell

(57) ABSTRACT

A check valve having a piston-like ball or stopper a predetermined distance from the valve seat so that the ball or stopper seats against the valve seat only under backflow pressure.

10 Claims, 2 Drawing Sheets

U.S. PATENT DOCUMENTS

| | | | |
|---|---|---|---|
| 4,869,715 A | 9/1989 | Sherburne | |
| 4,909,783 A | 3/1990 | Morrison | |
| 4,921,477 A | 5/1990 | Davis | |
| 4,922,902 A | 5/1990 | Wuchinich et al. | |
| 4,935,005 A | 6/1990 | Haines | |
| 4,989,583 A | 2/1991 | Hood | |
| 5,061,241 A | 10/1991 | Stephens et al. | |
| 5,154,694 A | 10/1992 | Kelman | |
| 5,261,883 A | 11/1993 | Hood et al. | |
| 5,322,504 A | 6/1994 | Doherty et al. | |
| 5,358,150 A | 10/1994 | Scheuble et al. | |
| 5,359,996 A | 11/1994 | Hood | |
| 5,380,280 A | 1/1995 | Peterson | |
| 5,514,088 A | 5/1996 | Zakko | |
| 5,514,110 A * | 5/1996 | Teh | 137/517 |
| 5,562,692 A | 10/1996 | Bair | |
| 5,577,533 A | 11/1996 | Cook | |
| 5,616,120 A | 4/1997 | Andrew et al. | |
| 5,735,815 A | 4/1998 | Bair | |
| 5,741,229 A | 4/1998 | Robinson et al. | |
| 5,853,384 A | 12/1998 | Bair | |
| 5,865,790 A | 2/1999 | Bair | |
| 5,885,243 A | 3/1999 | Capetan et al. | |
| 5,989,212 A | 11/1999 | Sussman et al. | |
| 5,997,499 A * | 12/1999 | Sussman et al. | 604/27 |
| 6,004,284 A | 12/1999 | Sussman et al. | |
| 6,080,128 A | 6/2000 | Sussman et al. | |
| 6,110,162 A | 8/2000 | Sussman et al. | |
| 6,123,101 A * | 9/2000 | Velie et al. | 137/517 |
| 6,155,975 A | 12/2000 | Urich et al. | |
| 6,179,805 B1 | 1/2001 | Sussman et al. | |
| 6,179,808 B1 | 1/2001 | Boukhny et al. | |
| 6,186,148 B1 | 2/2001 | Okada | |
| 6,196,989 B1 | 3/2001 | Padget et al. | |
| 6,206,848 B1 | 3/2001 | Sussman et al. | |
| 6,241,700 B1 | 6/2001 | Leukanech | |
| 6,258,111 B1 | 7/2001 | Ross et al. | |
| 6,287,274 B1 | 9/2001 | Sussman et al. | |
| 6,315,755 B1 | 11/2001 | Sussman | |
| 6,331,171 B1 | 12/2001 | Cohen | |
| 6,398,759 B1 | 6/2002 | Sussman | |
| 6,425,883 B1 | 7/2002 | Urich et al. | |
| 6,440,103 B1 | 8/2002 | Hood et al. | |
| 6,513,545 B2 | 2/2003 | Rhone | |
| 6,575,929 B2 | 6/2003 | Sussman et al. | |
| 6,575,990 B1 | 6/2003 | Wang et al. | |
| 6,579,270 B2 | 6/2003 | Sussman et al. | |
| 6,589,201 B1 | 7/2003 | Sussman et al. | |
| 6,589,204 B1 | 7/2003 | Sussman et al. | |
| 6,623,477 B1 | 9/2003 | Elbrecht et al. | |
| 6,648,847 B2 | 11/2003 | Sussman et al. | |
| 6,676,628 B2 | 1/2004 | Sussman et al. | |
| 6,796,957 B2 | 9/2004 | Carpenter et al. | |
| 6,830,064 B2 | 12/2004 | Ji | |
| 6,860,868 B1 | 3/2005 | Sussman et al. | |
| 6,892,756 B2 * | 5/2005 | Schulze | 137/517 |
| 6,920,895 B2 * | 7/2005 | Avis et al. | 137/517 |
| 6,921,385 B2 | 7/2005 | Clements et al. | |
| 6,953,052 B2 * | 10/2005 | Lehtonen | 137/517 |
| 7,160,268 B2 | 1/2007 | Darnell et al. | |
| 7,509,831 B2 | 3/2009 | Khashayar | |
| 7,535,815 B2 | 5/2009 | Van Den Homberg et al. | |
| 2002/0013572 A1 | 1/2002 | Berlin | |
| 2002/0161326 A1 | 10/2002 | Sussman et al. | |
| 2002/0188261 A1 | 12/2002 | Hruska | |
| 2003/0195538 A1 | 10/2003 | Wang et al. | |
| 2004/0024380 A1 | 2/2004 | Darnell et al. | |
| 2004/0082939 A1 | 4/2004 | Berlin | |
| 2005/0228423 A1 | 10/2005 | Khashayar | |
| 2005/0228424 A1 | 10/2005 | Khashayar | |
| 2006/0058823 A1 | 3/2006 | Dimalanta et al. | |
| 2006/0161101 A1 | 7/2006 | Dimalanta et al. | |
| 2006/0173403 A1 | 8/2006 | Injer | |
| 2006/0184091 A1 | 8/2006 | Dimalanta et al. | |
| 2006/0212037 A1 | 9/2006 | Sussman et al. | |
| 2006/0212039 A1 | 9/2006 | Sussman et al. | |
| 2006/0224116 A1 | 10/2006 | Underwood et al. | |
| 2008/0073906 A1 | 3/2008 | Turner | |
| 2008/0077077 A1 | 3/2008 | Williams | |
| 2008/0082077 A1 | 4/2008 | Williams | |
| 2008/0086093 A1 | 4/2008 | Steppe et al. | |
| 2008/0125697 A1 | 5/2008 | Gao | |
| 2009/0032121 A1 | 2/2009 | Chon | |
| 2009/0032123 A1 | 2/2009 | Bourne | |
| 2009/0068870 A1 | 3/2009 | Mezhinsky | |

FOREIGN PATENT DOCUMENTS

| | | |
|---|---|---|
| WO | WO 2006/101727 A2 | 9/2006 |
| WO | WO 2006/101727 A3 | 9/2006 |

\* cited by examiner

Surgical Handpiece 201

FIG. 2

(Prior Art)

CHECK VALVE

BACKGROUND OF THE INVENTION

This invention relates generally to the field of cataract surgery and more particularly to a check valve for use in a handpiece for practicing the liquefaction technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted with the injection of the heated solution and the injection of a relatively cool solution, thereby quickly cooling and removing the heated solution. This technique is more fully described in U.S. Pat. No. 5,616,120 (Andrew, et al.), the entire contents of which is incorporated herein by reference. A commercially available handpiece used to practice this cataract removal technique is described in U.S. Pat. No. 6,860,868 (Sussman, et al.) and sold as the AQUALASE® handpiece by Alcon Laboratories, Inc., Fort Worth, Tex. The handpiece disclosed in this reference (e.g., handpiece 201 as seen in FIG. 2) uses a check valve to prevent the pressurized pulses of heated fluid from being forced backwards through the handpiece toward the irrigation fluid source. The check valve has a stopper or ball that is pressed against a valve seat by a spring, so that the valve is normally closed at ambient conditions. The inventors have found that during autoclaving, mineral residue from the irrigation fluid can build up around the stopper and seat, affecting the performance of the check valve. In addition, check valves that are closed completely require some initial force to open, thereby reducing the efficiencies of the handpiece at lower operating pressures, and making the check valve very sensitive to the spring rate and load force variability.

Therefore, a need continues to exist for a check valve with increased performance and reduces sensitivity to spring rate, load force variability and mineral deposits.

BRIEF SUMMARY OF THE INVENTION

The present invention improves upon the prior art by providing a check valve having a piston-like ball or stopper a pre-determined distance from the valve seat so that the ball or stopper seats against the valve seat only under backflow pressure.

Accordingly, one objective of the present invention is to provide a check valve having a piston-like ball or stopper.

Another objective of the present invention is to provide a check valve that seals only under backflow pressure.

These and other advantages and objectives of the present invention will become apparent from the detailed description and claims that follow.

BRIEF DESCRIPTION OF THE DRAWINGS

The FIG. 1 is a cross-sectional view of the check valve of the present invention.

Figure 2:
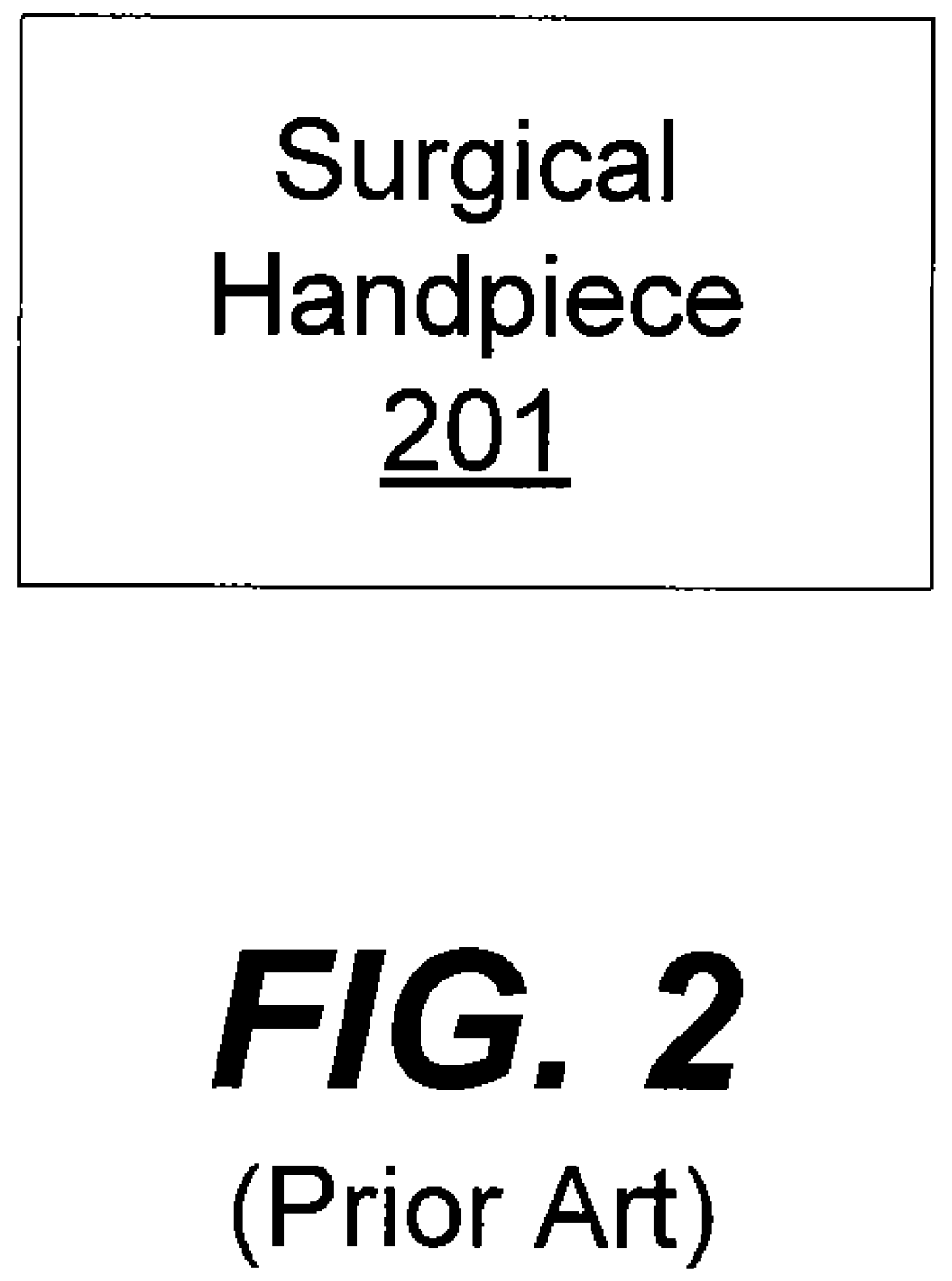

FIG. 2 illustrates a block diagram for a surgical handpiece.

DETAILED DESCRIPTION OF THE INVENTION

Figure 1:
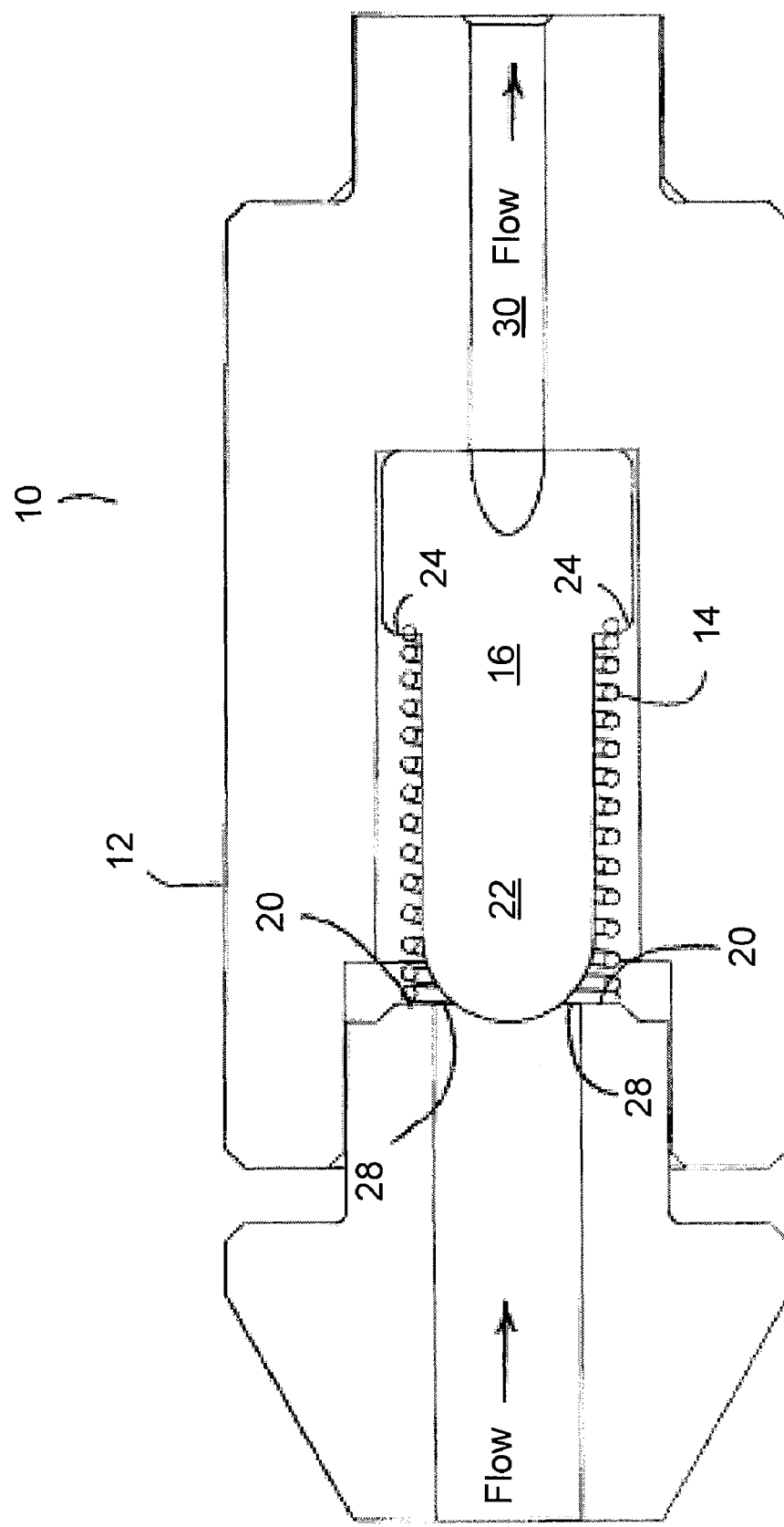

As seen in FIG. 1, check valve 10 of the present invention generally includes hollow housing 12, spring 14 and ball or stopper 16. Formed within housing 12 is valve seat 20. Housing 12, upstream spring 14 and stopper 16 are all constructed of conventional materials well-known in the art. Spring 14 extends over stem 22 of stopper 16 and presses against surface 24 of stopper 16 and valve seat 20 of housing 12 so as to bias stopper 16 away from valve seat 20. At ambient pressure conditions, the strength of spring 14 is sufficient to prevent stopper 16 from sealing against seat 20 and forming small gap 28. The relative strength of spring 14 is such that any back pressure in downstream tube 30 pushes against stopper 16 and overcomes the biasing function of spring 14 so that stopper 16 seals against seat 20. When the back pressure is removed, spring 14 once against pushes stopper 16 away from seat 20, forming gap 28. Such a construction allows check valve 10 to remain open except when there is pressurized fluid in downstream tube 30, but check valve 10 closes quickly once pressurized fluid builds in downstream tube 30. Any pressurized fluid must travel the relatively long length (approximately 2.8 mm) of stem 22 of stopper 16 prior to escaping out of gap 28. Such a long travel time allows additional time for the back pressure to push to push stopper 16 against seat 20 and close gap 28 before any backflow of fluid can escape out of gap 28.

This description is given for purposes of illustration and explanation. It will be apparent to those skilled in the relevant art that changes and modifications may be made to the invention described above without departing from its scope or spirit.

I claim:

1. A surgical handpiece used to perform liquefaction during a cataract procedure, comprising:
    a hollow housing having a stem valve seat;
    a stopper configured to reciprocate within the hollow housing, the stopper comprising:
        a piston head,
        an extended stem coupled to the piston head; and
    a spring extending along the stem to engage the piston head to bias the piston head away from the stem valve seat so as to form a gap between the stem valve seat and the stem when a first pressure on the piston head provides an opposing force on the piston head that is less than a force provided on the piston head by the spring;
    wherein when a second pressure of pressurized pulses of heated fluid on the piston head provides an opposing force on the piston head that is greater than the force provided on the piston head by the spring, a length of the stem prevents flow of the pressurized pulses of heated fluid flowing along the stem from flowing past the stem valve seat before the stem seals against the stem valve seat;

wherein an end of the stem that seals against the valve seat is rounded;

wherein at least part of the rounded end of the stem is configured to extend past the stem valve seat when the piston head is biased against a side of the valve opposite the stem valve seat by the spring during the first pressure.

2. The surgical handpiece of claim 1, wherein the stem is approximately 2.8 mm.

3. The surgical handpiece of claim 1, wherein the stem is at least 2.8 mm.

4. The surgical handpiece of claim 1, wherein the head comprises a channel to allow flow in the first direction through the head when the piston head is biased away from the stem valve seat and against the hollow housing by the spring during the first pressure.

5. The surgical handpiece of claim 1, wherein the stem is solid and does not include a flow-through passage.

6. The surgical handpiece of claim 1, wherein the spring is configured to bias the piston head away from the stem valve seat by biasing the piston head in a first direction in the presence of fluid flow in the first direction and wherein the stem is configured to seal against the stem valve seat when the second pressure, caused by fluid flow in a backflow direction that is opposite the first direction, on the piston head provides an opposing force on the piston head that is greater than the force provided on the piston head by the spring.

7. A check valve, comprising:
a hollow housing having a stem valve seat;
a stopper configured to reciprocate within the hollow housing, the stopper having a stem that is configured to contact and seal against the stem valve seat, wherein the stopper further comprises a head coupled to the stem; and
a spring extending along the stem to engage the head to bias the stopper in a first direction away from the stem valve seat so as to form a gap between the stem valve seat and the stem when a first pressure on the head provides an opposing force on the stopper that is less than a force provided on the stopper by the spring, wherein biasing the stopper in the first direction comprises the spring pressing the head against a side of the valve opposite the stem valve seat and wherein the head comprises at least one channel to allow flow in the first direction through the check valve when pressed against the side of the valve opposite the stem valve seat;

wherein when a second pressure on the head provides a force on the stopper that is greater than the force provided on the stopper by the spring, a length of the stem prevents fluid flowing at the second pressure along the stem from flowing past the stem valve seat before the stem seals against the stem valve seat;

wherein an end of the stem that seals against the valve seat is rounded; and wherein at least part of the rounded end of the stem is configured to extend past the stem valve seat when the head is biased against the side of the valve opposite the stem valve seat by the spring.

8. The check valve of claim 7, wherein the check valve is configured to be used in a surgical handpiece to prevent pressurized pulses of heated fluid from being forced backwards through the handpiece toward an irrigation fluid source coupled to the handpiece.

9. The check valve of claim 7, wherein the stem is solid and does not include a flow-through passage.

10. The check valve of claim 7, wherein the spring is configured to bias the stopper in the first direction away from the stem valve seat in the presence of fluid flow in the first direction and wherein the stem is configured to seal against the stem valve seat when the second pressure, caused by fluid flow in a backflow direction that is opposite the first direction, on the head provides an opposing force on the head that is greater than the force provided on the head by the spring.

* * * * *